United States Patent [19]

Chandrakumar et al.

[11] Patent Number: 5,604,220

[45] Date of Patent: Feb. 18, 1997

[54] TARTARIC ACID DERIVATIVES OF SUBSTITUTED DIBENZOXAZEPINE COMPOUNDS, PHARMACEUTICAL COMPOSITIONS AND METHODS OF USE

[75] Inventors: Nizal S. Chandrakumar, Vernon Hills; Richard A. Mueller, Glencoe, both of Ill.

[73] Assignee: G. D. Searle & Company, Chicago, Ill.

[21] Appl. No.: 407,512

[22] Filed: Mar. 14, 1995

Related U.S. Application Data

[62] Division of Ser. No. 134,345, Oct. 7, 1993, Pat. No. 5,424,424.

[51] Int. Cl.$^6$ .................................................. A61K 31/55
[52] U.S. Cl. ........................................................ 514/211
[58] Field of Search ............................................ 514/211

[56] References Cited

U.S. PATENT DOCUMENTS

| | | | |
|---|---|---|---|
| 2,852,528 | 9/1958 | Hoffmann et al. | 260/327 |
| 3,210,372 | 10/1965 | Werner et al. | 260/309.6 |
| 3,357,998 | 12/1967 | Cusic et al. | 260/333 |
| 3,534,019 | 10/1970 | Coyne et al. | 260/239 |
| 3,624,104 | 11/1971 | Cusic et al. | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,290,953 | 9/1981 | Koizumi et al. | 260/333 |
| 4,379,150 | 4/1983 | Ito et al. | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1987 | Mueller | 540/547 |
| 4,704,386 | 11/1987 | Mueller | 514/211 |
| 5,180,720 | 1/1993 | Husa et al. | 514/211 |
| 5,182,272 | 1/1993 | Hallinan et al. | 514/211 |
| 5,189,033 | 2/1993 | Tucker | 540/488 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinlan et al. | 514/80 |
| 5,288,719 | 2/1994 | Husa et al. | 514/211 |
| 5,304,644 | 4/1994 | Husa et al. | 540/547 |
| 5,317,101 | 3/1994 | Oldfield et al. | 540/488 |
| 5,324,722 | 6/1994 | Hagen et al. | 514/211 |
| 5,345,746 | 10/1994 | Chandrakumar et al. | 514/211 |
| 5,354,747 | 10/1994 | Hansen et al. | 514/211 |
| 5,354,863 | 10/1994 | Dappen et al. | 546/35 |
| 5,424,424 | 6/1995 | Chandrakumar et al. | 540/488 |

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0480641 | 4/1992 | European Pat. Off. | C07D 223/20 |
| 0534667 | 3/1993 | European Pat. Off. | C07D 417/06 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom | C07D 267/20 |
| WO92/19617 | 11/1992 | WIPO | C07D 413/12 |
| WO93/07132 | 4/1993 | WIPO | C07D 267/20 |
| WO93/09104 | 5/1993 | WIPO | C07D 267/20 |

OTHER PUBLICATIONS

A. Bennett, et al., "*Antagonism of Prostanoid–Induced Contractions of Rat Gastric Fundus Muscle by SC–19220 Sodium Meclofenamate, Indomethacin or Trimethoquinol,*" Br. J. Pharmac., 71, 169–175 (1980) –London.

W. E. Coyne, et al. "*Anticonvulsant Semicarbazides,*" J. Med. Chem., 11(6), 1158–1160 (1968) –USA.

E. J. Drower, et al. "The Antiociceptive Effects of Prostaglandin Antagonists in the Rat," European Journal of Pharmacology, 133, 249–256 (1987) –Europe.

F. R. George, et al. "Antagonism of Alcohol Hypnosis by Blockade of Prostaglandin Synthesis and Activity: Genotype and Time Course Effects," Pharmacology, Biochemistry & Behavior, vol. 19, 131–136 (1983) –USA.

R. Gimet, et al. "Quantitative Determination of Polymorphic Forms in a Formulation Matrix Using the Near Infra-Red Reflectance Analysis Technique," Journal of Pharmaceutical & Biomedical Analysis, vol. 5, No. 3, 205–211 (1987) –Great Britain.

A. Gomes, et al. "Pharmacodynamics of Venom of the Centipede *Scolopendra Subspinipes Dehaani,*" Indian Journal of Experimental Biology, vol. 20, 615–618, Aug. (1982) –India.

(List continued on next page.)

*Primary Examiner*—Robert T. Bond
*Attorney, Agent, or Firm*—Fitzpatrick, Cella, Harper & Scinto

[57] ABSTRACT

The present invention provides substituted dibenzoxazepine compounds of Formula I:

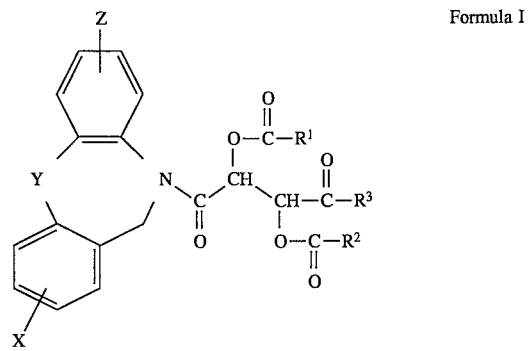

Formula I which are useful as analgesic agents for the treatment of pain, and as prostaglandin-$E_2$ antagonists for the treatment of prostaglandin-$E_2$ mediated diseases, pharmaceutical compositions comprising a therapeutically-effective amount of a compound of Formula I in combination with a pharmaceutically-acceptable carrier, a method for eliminating or ameliorating pain in an animal, and a method for treating prostaglandin-$E_2$ mediated diseases in an animal, comprising administering a therapeutically-effective amount of a compound of Formula I to the animal.

4 Claims, No Drawings

OTHER PUBLICATIONS

K. Gyires, et al. "The Use of the Writhing Test in Mice for Screening Different Types of Analgesics," *Arch. Int. Pharmacodyn,* 267, 131–140 (1984) –USA.

D. E. MacIntyre, et al. "Antagonism of Human Platelet Responses to Stimulatory and Inhibitory Prostaglandins," *Prog. Lipid. Res.,* 20 (1–4), 453–9 (1981) –USA.

C. A. Maggi, et al. "The Effect of SC–19220, a Prostaglandin Antagonist, on the Micturition Reflex in Rats," *European Journal of Pharmacology,* 152, 273–279 (1988) –Europe.

K. Nagarajan, et al. "Synthesis of 10, 11–Dihydrodibenz[b, f][1,4]oxazepine Derivatives as Potential Anticonvulsant & Psychotropic Agents," *Indian Journal of Chemistry,* vol. 24B, 840–844 (1985) –India.

S. Nakajyo, et al. "Inhibitory Effect of Bassianolide, a Cyclodepsipeptide, on Drug–Induced Contractions of Isolated Smooth Muscle Preparations," *Japan J. Pharmacol.,* 32, 55–64 (1982) –Japan.

A. Rakovska, et al. "Antagonistic Effect of SC–19220 on the Responses of Guinea–Pig Gastric Muscles to Prostaglandins $E_1$, $E_2$, and $F_{2\alpha}$," *Arch. Int. Pharmacodyn.,* 268, 59–69 (1984) –USA.

J. H. Sanner "Dibenzoxazepine Hydrazides as Prostaglandin Antagonists," *Intra–Science Chem. Rept.,* vol. 6, No. 1, 1–9 (1972) –USA.

J. H. Sanner, et al. "Structure–Activity Relationships of Some Dibenzoxazepine Derivatives as Prostaglandin Antagonists," *Advances in the Biosciences,* 9, 139–148 (1972) –USA.

TARTARIC ACID DERIVATIVES OF SUBSTITUTED DIBENZOXAZEPINE COMPOUNDS, PHARMACEUTICAL COMPOSITIONS AND METHODS OF USE

This is a DIVISIONAL application of application Ser. No. 08/134,345, filed on Oct. 7, 1993, U.S. Pat. No. 5,424,424.

BACKGROUND OF THE INVENTION

(1) Field of the Invention

The present invention generally relates to compounds having pharmacological activity which are useful as pharmaceutical agents and, more particularly, as analgesic agents for the treatment of pain, and as prostaglandin-$E_2$ antagonists for the treatment of prostaglandin-$E_2$ mediated diseases, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain and prostaglandin-$E_2$ mediated diseases employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever and inflammation, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are not opiates, salicylates or nonsteroidal antiinflammatory agents, and represent another class of compounds which are useful as analgesic agents.

(2) Description of the Related Art

PCT US92/08103 discloses substituted dibenzoxazepine compounds in which the 2-, 3-, 5-, 8- and/or the side chain is substituted.

U.S. Pat. No. 3,357,998 discloses derivatives of dihydrodibenz[b,f][1,4]oxazepine-10-carboxylic acids.

U.S. Pat. No. 4,170,593 discloses 1-(substituted amino)alkanoyl-2-(dibenzoxazepine-10-carbonyl) hydrazines and derivatives thereof.

U.S. Pat. No. 4,614,617 discloses intermediates for 8-chlorodibenz[b,f][1,4]oxazepine-10(11H)carboxylic acid, 2-(sulfinyl- and sulfonyl-containing acyl)hydrazides.

U.S. Pat. No. 4,681,939 discloses 8-chlorodibenz[b,f][1,4]oxazepine-10(11H)carboxylic acid, 2-[(substituted phenylsulfinyl)alkanoyl]-hydrazides and 8-chlorodibenz[b,f][1,4]oxazepine-10(11H)carboxylic acid, 2-[(substituted phenylsulfonyl)alkanoyl]-hydrazides.

U.S. Pat. No. 4,290,953 discloses dibenz[b,f][1,4]oxazepine derivatives which are stated to have serum cholesterol lowering activity, serum lipid lowering activity, blood lipid peroxide lowering activity and antiaggregation of platelet activity.

U.S. Pat. No. 4,379,150 discloses dibenz[b,f][1,4]oxazepine derivatives which may have a heterocyclic ring present in the side chain at the 10-position of the molecule.

Each of the documents described hereinabove discloses compounds which are structurally different from the compounds of the present invention. Thus, the compounds of the present invention are structurally distinct from that which has been described in the art.

SUMMARY OF THE INVENTION

The present invention provides compounds having a structure of Formula I:

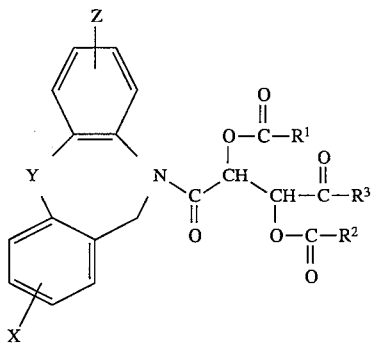

Formula I or a pharmaceutically-acceptable salt thereof, wherein:

X is hydrogen or halogen;

Y is oxygen, sulfur,

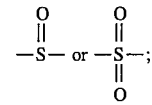

Z is hydrogen, halogen or —$CF_3$;

$R^1$, $R^2$ and $R^4$ may be the same or different, and are hydrogen or alkyl;

$R^3$ is —OH, —O-alkyl or —$NR^4$-alkylene-$R^5$; and $R^5$ is —$NR^1R^2$ or aryl.

The present invention also provides pharmaceutical compositions which are pharmaceutically acceptable and which comprise a therapeutically effective amount of a compound of Formula I in combination with a pharmaceutically-acceptable carrier, and a method for eliminating or ameliorating pain in an animal, or for treating a prostaglandin mediated disease, comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes one, two or three carbon atoms, which can be a straight or branched chain. Representative of such radicals are methyl, ethyl, propyl, isopropyl, butyl, sec-butyl, isobutyl, tert-butyl, pentyl and the like.

The term "alkylene" as used herein means a straight or branched saturated hydrocarbon chain spacer arm which has from one to ten carbon atoms, and within which includes from one to six carbon atoms, and further within which includes one, two or three carbon atoms.

The term "analgesia" as used herein means the reduction, or absence, of sensibility to pain, designating particularly the relief of pain without loss of consciousness.

The term "animal" as used herein includes mammals and nonmammals, and further includes humans and nonhuman mammals.

The term "aryl" as used herein means 5- or 6-membered single-ring aromatic radicals which may include from zero to four heteroatoms selected from nitrogen, sulfur or oxygen, and within which includes from zero to two heteroatoms, and further within which includes from zero to one heteroatom. Representative aryl groups include phenyl, thienyl, furanyl, pyridinyl, imidazolyl, thiazolyl, pyrimidinyl, pyrazinyl, pyridazinyl, napthoyl, (is)oxazolyl, triazolyl, tetrazolyl, pyrrolyl, pyridinyl-N-oxide and the like.

The abbreviation "Boc" as used herein means t-butyloxycarbonyl.

The term "carbonyl" as used herein means a

group.

The term "carboxy" as used herein means a

group.

The term "composition" as used herein means a product which results from the combining of more than one element or ingredient.

The abbreviation "DMAP" as used herein means 4-(N,N-dimethylamino)pyridine.

The abbreviation "DMF" as used herein means dimethylformamide.

The phrase "$EC_{50}$ concentration" as used herein means that concentration of a compound or drug which produces 50% of a maximal biological effect, such as contractions in isolated segments of guinea pig ileum.

The phrase "$ED_{50}$ dose" as used herein means that dose of a compound or drug which produces a biological effect, such as producing analgesia, in 50% of the animals to which the compound or drug was administered.

The abbreviation "DR" as used herein means dose ratio.

The abbreviation "Et" as used herein means ethyl ($—CH_2CH_3$).

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The term "halo" or "halogen" as used herein means chlorine (Cl), bromine (Br), fluorine (F) and/or iodine (I).

The term "heteroatom" as used herein means an atom of any element other than carbon or hydrogen, such as nitrogen, oxygen or sulfur.

The abbreviation "$^1H$ NMR" as used herein means Proton Nuclear Magnetic Resonance.

The abbreviation "HPLC" as used herein means High Pressure Liquid Chromatography, which is the same as High Performance Liquid Chromatography.

The term "hydroxy" as used herein means the group —OH.

The term "intragastrically" and/or the abbreviation "i.g." as used herein mean that a compound or drug was administered into the stomach.

The abbreviation "i.p." as used herein means that a compound or drug was administered intraperitoneally.

The abbreviation "IR" as used herein means infrared (referring to an infrared spectrum).

The abbreviation "LAH" as used herein means lithium aluminum hydride.

The abbreviation "Me" as used herein means methyl ($—CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laureate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "Pr" as used herein means propyl.

The abbreviation "p.o." as used herein means that a compound or drug was administered orally.

The phrase "protecting group" as used herein means substituents which protect the reactive functional group from undesirable chemical reactions, including decomposition. Examples of such protecting groups include esters of carboxylic acids or alcohols, ethers of alcohols and acetals and ketals of aldehydes and ketones.

The phrase "N-protecting group" or "N-protected" as used herein means those groups intended to protect an amine or the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy, benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to it means that compound, product or material whose chemical name is given, and/or whose structure is shown, in the particular example, or subpart thereof, in which it appears.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the 1-, 2-, 3-, 4.-, 5-, 6-, 7-, 8-, 9- and/or 10-position is substituted.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. For example, it is known that tartaric acid has two asymmetric carbon atoms which result in the DL form and three isomeric forms, which are the d-form, the corresponding l-form and the meso form. All such isomers, as well as mixtures thereof, are intended to be included in this invention, and are intended to be included within Formula I.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laureate, benzoate, lactate, phosphate, tosylate, citrate, maleate, fumarate, succinate, tartrate, naphthoate, mesylate, glucoheptonate, lactobionate, and laurylsulphonate salts and the like. (See, for example, S. M. Berge et al., "Pharmaceutical Salts," *J Pharm. Sci.*, 66, 1–19. (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary, tertiary or quaternary amine. Representative alkali or alkaline earth salts include the lithium, sodium, potassium, calcium, magnesium, and aluminum salts and the like. Representative organic amines useful for the formation of base addition salts include ethylamine, tetramethyl-ammonium hydroxide, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal, sublingual, transdermal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are the compounds shown and described in Examples 3, 4, 5, 7, 8 and 9 hereinbelow. The most preferred embodiment of this invention is the compound shown and described in Example 4 hereinbelow.

(3) Utility

Compounds within the present invention have been found to exhibit activity as prostaglandin $E_2$ antagonists (antagonists of prostaglandins of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating prostaglandin-$E_2$ mediated diseases, such as convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin antagonists.

The compounds of this invention can also behave as prodrugs for the tartaric acid derivatives wherein an ester is administered to a mammal. The ester is hydrolyzed by mammalian enzymes in, for example, the gut, liver, blood or other metabolizing organs.

(4) Methods of Preparation

In general, the compounds of the present invention may be prepared by the methods illustrated in the following general reaction scheme, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, salicaldehyde or the corresponding mercapto compound (wherein X is hydrogen or halogen) is reacted with base and to this is added a substituted 2-chloronitrobenzene (wherein Z is hydrogen, halogen or —$CF_3$). The resulting ether or thioether is reduced to yield substituted dibenz[b,f][1,4]oxazepine or sulfur analog, wherein X and Z are as described hereinabove, and wherein Y is oxygen or sulfur.

The heterocyclic base IV in General Reaction Scheme No. 1 is then treated with a tartaric acid derived cyclic anhydride in a non-protic solvent at a temperature of between about $-40°$ C. to solvent reflux temperature, preferably at or about room temperature to provide the acid V. In addition, a base can be used if desired, but the preferred conditions are without added base.

The tartaric acid derived starting materials in General Reaction Scheme No. 1 are prepared by acylation and subsequent dehydration of tartaric acid by methods well known to those skilled in the art. Acylating agents such as acid anhydrides, acid halides or ketenes can be used. Dehydration, i.e., removal of the elements of water, to provide the tartaric anhydride derivatives is accomplished during the process of acylation or by reagents, such as phosphorus pentoxide, phosphorus oxychloride and the like. The acylation/dehydration process can be carried out using an acylating agent, e.g., acetic anhydride, as a solvent if it is a liquid, or with a non-protic or dipolar aprotic co-solvent or solvent mixture, such as methylene chloride, tetrahydrofurane, toluene, DMF, acetonitrile, dimethoxyethane or the like. Reaction temperatures can vary from $-40°$ C. to the reflux temperature of the solvent or reagent, but are preferably from about room temperature to $140°$ C.

The carboxylic acids (Compound V, General Reaction Scheme No. 1) can be converted into the amides or esters of this invention by a number of methods well known to those skilled in the art including, for example, conversion of V into it's acid chloride or bromide or mixed anhydride derivative followed by treatment with primary or secondary amine or by an alcohol or the metal salt of an alcohol with or without added organic or inorganic base. Organic bases (see discussion below) are preferred. Examples of reagents for forming acid halides are thionyl chloride, thionyl bromide, oxalyl chloride and the like. Mixed anhydrides are readily formed using, for example, isobutylchloroformate, benzyl chloroformate and the like in the presence of a base such an N-methyl morpholine, triethylamine, 2,6-diisopropylpiperidine, 4-(N,N-dimethylamino)-pyridine (DMAP) and the like either as pure reagents or as mixtures. For example, a catalytic amount of DMAP with triethylamine is a combination of organic bases well known to those skilled in the art. Reaction temperatures can vary from $-50°$ C. to solvent reflux. Solvents can be non-protic or dipolar aprotic such as THF, ethyl acetate, methylene chloride, DMF, acetonitrile, ether, and the like used as pure solvents or mixtures and the reaction carried out under an atmosphere of air, including dry air, or an inert gas at atmospheric or increased pressure. Preferred reagents for the compounds of this invention are isobutyl chloroformate with N-methylmorpholine to form the mixed anhydride (General Reaction Scheme No. 1) at a temperature of about $0°$ C. in THF under an atmosphere of nitrogen or argon at atmospheric pressure.

Following, for example, mixed anhydride formation, the amide or ester products of this invention are formed by addition of an alcohol, metal salt of the alcohol or amine. This conversion can be accomplished with or without added base under normal atmosphere or an inert gas atmosphere using increased pressure or at atmospheric pressure at a temperature from about −20° C. to solvent reflux. Solvents for these reactions are as discussed above for mixed anhydride formation. In addition, this step can be carried out either separately or in the same reaction vessel as, for example, mixed anhydride formation. Preferred conditions are the use of THF solvent at about 0° C. under nitrogen or argon at atmospheric pressure in the same reaction vessel as, for example, mixed anhydride formation occurred wherein reactive intermediates are not isolated.

Conversion of the sulfide heterocycles of this invention into their sulfoxide or sulfone derivatives (Y=—SO— or —SO$_2$—) are carried out on IV, V or the amides or esters using oxidation reagents well known to those skilled in the art and shown in General Reaction Scheme No. 1. Examples of such reagents include hydrogen peroxide, bleach, tert-butyl hypochlorite, oxygen or periodate salts or acid. About one oxidizing equivalent is used to form sulfoxides and two or more to form sulfones. Solvents, or solvent mixtures, can be protic, non-protic or dipolar aprotic. Non-protic and dipolar aprotic solvents are discussed above. Protic solvents can include, for example, water and alcohols such as methanol, ethanol, isopropanol and the like. Temperatures can be from about −20° C. to room temperature or higher with about 0° C. preferred for sulfoxide formation and room temperature preferred for sulfone formation. Either an atmosphere of air, argon or nitrogen can be used with air at atmospheric pressure, which is preferred when hydrogen peroxide is used as the preferred oxidizing agent.

In the resulting compounds, $R^1$, $R^2$ and $R^4$ may be the same or different, and are hydrogen or alkyl; $R^3$ is —OH, —O-alkyl or —NR$^4$-alkylene-R$^5$; and $R^5$ is —NR$^1$R$^2$ or aryl.

GENERAL REACTION SCHEME NO. 1

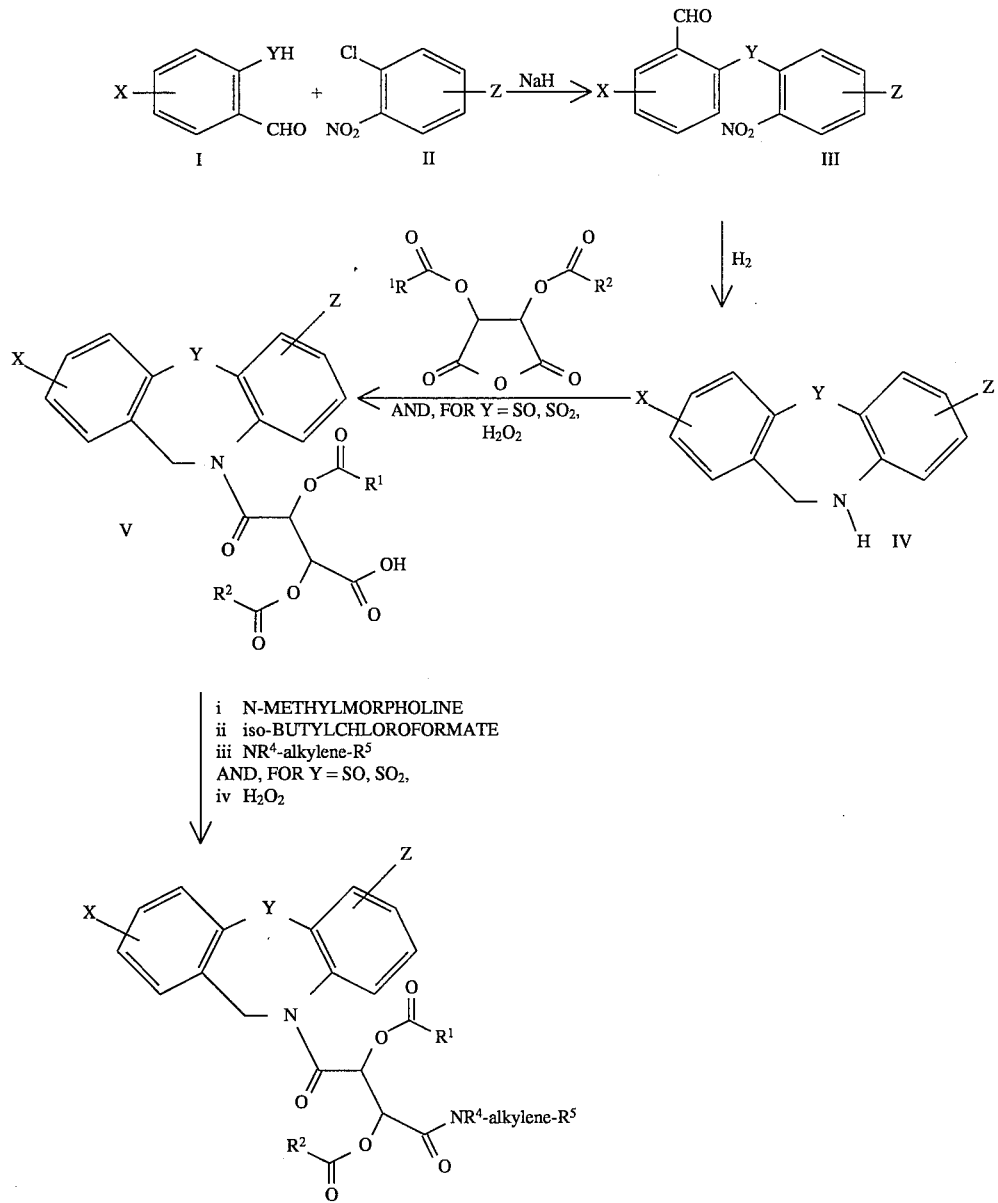

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BBA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal, sublingual or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly-(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

Unless indicated otherwise in a particular example, all of the starting materials, and all of the equipment, employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), TCI American Tokyo Kasei, Inc. (Atlanta, Ga.) and Chemical Dynamics Corp. (South Plainfield, N.J.). Most of the starting materials were obtained from Aldrich Chemical Co. (Milwaukee, Wis.). The syntheses of those starting materials which are not commercially available are described in the examples presented below.

All patents and publications referred to in the examples, and throughout the specification, are hereby incorporated herein by reference, without admission that such is prior art.

17

EXAMPLE 1

αS,βS-Bis(acetyloxy)-8-chloro-γ-dibenz[b,f][1,4]-
oxazepine-10(11H) -butanoic Acid

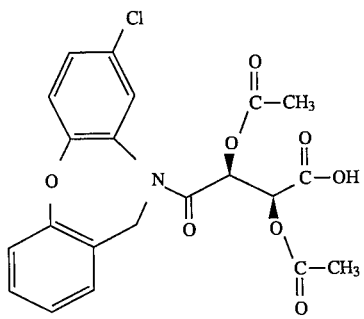

8-chloro-10,11-dihydrodibenz[b,f][1,4]oxazepine is synthesized in the manner described in U.S. Pat. No. 3,534,019, which is incorporated herein by reference.

Briefly, 200 parts of 2,5-dichloro-nitrobenzene were heated to 160° C. and stirred, and 160 parts of the potassium salt ore salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz[b,f][1,4]oxazepine melting at about 94°–95° C.

Diacetyl-D-tartaric anhydride is prepared from D-tartaric acid in the manner described in "DIACETYL-d-TARTARIC ANHYDRIDE (Tartaric anhydride, diacetate of d-)", *Organic Synthesis,* Collective Volume 4, 242–243 (1963). Briefly, a tartaric acid isomer or mixture of isomers is treated with acetic anhydride with a catalytic amount of sulfuric acid. The solution is heated gently for about 10 minutes and poured into an ice bath. The crystalline material formed is collected on a filter and is washed with toluene and ether and dried over phosphorus pentoxide and paraffin shavings. The crystalline bisacetyltartaric anhydride is used as is described in the following paragraph.

A mixture of 8-chloro-10,11-dihydrodibenz[b,f][1,4]oxazepine (2.33 g) and diacetyl-D-tartaric anhydride (2.16 g) was stirred in methylene chloride (20 mL) at room temperature. The solids dissolved quickly and, after approximately 5 minutes, precipitation started. After stirring for 16 hours, the mixture was filtered and the solid obtained was washed with ether to give 4.8 g of the title compound as a white solid.

18

$^1$H NMR (200 MHz, DMSO-$d_6$, 120° C.) d 1.86 (s, 3H), 1.92 (s, 3H), 4.79 (d, J=17 Hz, 1H), 5.08 (d, J=17 Hz, 1H), 5.15 (d, J=4.4 Hz, 1H), 5.76 (d, J=4.4 Hz, 1H), 7.01–7.29 (m, 4H), 7.35 (d, J=8.5 Hz, 1H), 7.46 (dd, J=8.5 Hz, 2.5 Hz, 1H), 7.52 (d, J=2.5 Hz, 1H).

EXAMPLE 2

αS,βS-Bis(actyloxy)-8-chloro-N-[2-(dimethylamino)-
ethyl]-γ-oxodibenz[b,f][1,4]oxazepine-10(11H)-
butanamide, Monohydrochloride

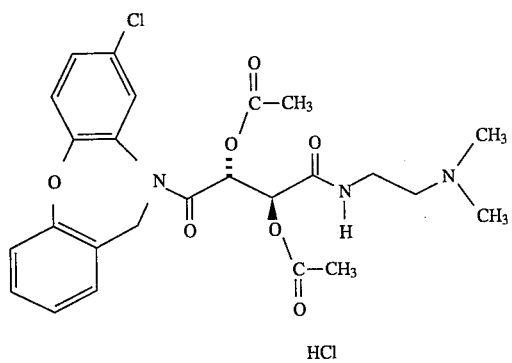

To a stirred solution of the title product of Example 1 (1 g) in tetrahydrofuran (10 mL) at 0° C. was added 4-methylmorpholine (0.246 mL) and isobutyl chloroformate (0.290 mL). After 20 minutes, N,N-dimethylethylenediamine (0.246 mL) was added. Stirring continued for 2 hours and then the volatiles were removed. The residue was extracted with ethyl acetate and water. The organic phase was washed successively with water, a saturated NaHCO3 solution and brine, dried over MgSO$_4$ and concentrated. The solid residue was shaken with ether and vacuum filtered and dried at room temperature in vacuo (1 mm Hg). To a solution of this solid (0.4 g) in chloroform (3 mL) was added a solution of hydrogen chloride in dioxane (7N, 1 mL). The volatiles were removed in vacuo, and the residue was dried at 78° C. in vacuo (1 mm Hg) to give the title compound as a white solid.

$^1$H NMR (200 MHz, DMSO-$d_6$) 1.80 (distorted broad singlet, 3H), 2.09 (distorted broad singlet, 3H), 2.72 (broad singlet, 6H), 3.03 (broad singlet, 2H), 3.35 (signal overlapped by H$_2$O, 2H), 4.33–6.0 (complex, 4H), 7.05–7.65 (complex, 7H), 8.40, 8.57, 8.75 (three broad singlets, 1H total).

Elemental Analysis data for $C_{25}H_{28}ClN_3O_7 \cdot HCl \cdot 0.5 H_2O$

| Calculated | | Found |
|---|---|---|
| 53.29 | C | 53.46 |
| 5.37 | H | 5.53 |
| 7.46 | N | 7.13 |
| 12.58 | Cl | 12.32 |

EXAMPLE 3

αS,βS-Bis(acetyloxy)-8-chloro-γ-oxo-N-(4-pyridinylmethyl)-dibenz[b,f][1,4]-oxazepine-10(11H Hydrochloride

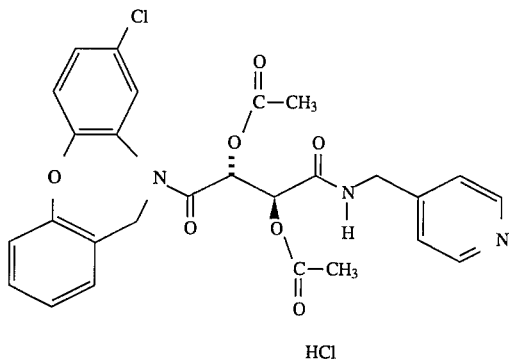

HCl

To a stirred solution of the title product of Example 1 (1 g) in tetrahydrofuran (10 mL) at 0° C. was added 4-methylmorpholine (0,246 mL) and isobutyl chloroformate (0.290 mL). After 20 minutes, 4-aminomethylpyridine (0,226 mL) was added. Stirring continued for 2 hours, and then the volatiles were removed. The residue was extracted with ethyl acetate and water. The organic phase was washed successively with water, a saturated $NaHCO_3$ solution and brine, dried over $MgSO_4$ and concentrated. The solid residue was shaken with ether and vacuum filtered and dried at room temperature in vacuo (1 mm Hg). To a solution of this solid (0.4 g) in chloroform (3 mL) was added a solution of hydrogen chloride in dioxane (7N, 1 mL). The volatiles were removed in vacuo and the residue was dried at 78° C. in vacuo (1 mm Hg) to give the title compound as a white solid with a purple tinge.

$^1$H NMR (200 MHZ, DMSO-$d_6$) 1.80 (broad singlet, 3H), 2.10 (broad singlet, 3H), 4.36–6.08 (complex, 6H), 7.05–7.60 (complex, 7H), 7.70, 7.79 (two broad singlet, 2H total), 8.82 (broad singlet, 2H), 8.99, 9.13, 9.42 (three broad singlets, 1H total).

Elemental Analysis data for $C_{27}H_{24}ClN_3O_7$. 0.8 HCl. 0.5 $H_2O$

| Calculated | | Found |
|---|---|---|
| 56.29 | C | 56.46 |
| 4.51 | H | 4.84 |
| 7.29 | N | 6.81 |
| 11.08 | Cl | 11.07 |

EXAMPLE 4

αS,βS-Bis(acetyloxy)-8-chloro-γ-oxo-N-(3-pyridinylmethyl)-dibenz[b,f][1,4]-oxazepine-10(11H Hydrochloride

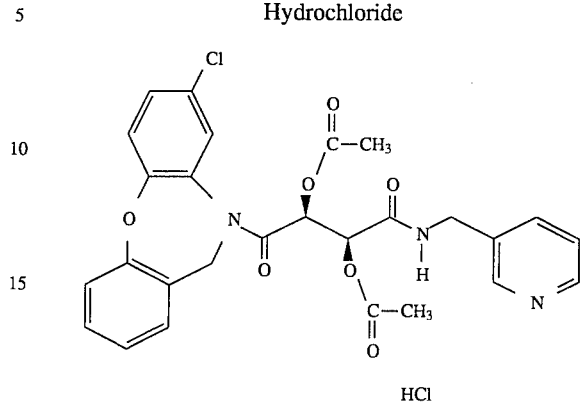

HCl

The procedure of Example 3 was repeated using 3-(aminomethyl)pyridine in the place of 4-(aminomethyl)pyridine to obtain the title compound as a white solid.

$^1$H NMR (200 MHz, DMSO-$d_6$) 1.77 (broad, distorted singlet, 3H), 2.03 (broad, distorted singlet, 3H), 4.35–6.07 (complex, 6H), 7.06–7.60 (complex, 7H), 7.97 (broad singlet, 1H), 8.24, 8.34 (two broad singlets, 1H total), 8.67, 8.78 (two broad singlets, 2H), 8.93, 9.10, 9.43 (three broad singlets, 1H total).

Elemental Analysis data for $C_{27}H_{24}ClN_3O_7$. 0.9 HCl. 1.25 $H_2O$

| Calculated | | Found |
|---|---|---|
| 54.66 | C | 54.77 |
| 4.66 | H | 4.20 |
| 7.08 | N | 7.03 |
| 11.35 | Cl | 11.22 |

EXAMPLE 5

αS,βS-Bis(acetyloxy)-8-chloro-γ-oxo-N-(2-pyridinylmethyl)dibenz[b,f][1,4]-oxazepine-10(11H) Hydrochloride

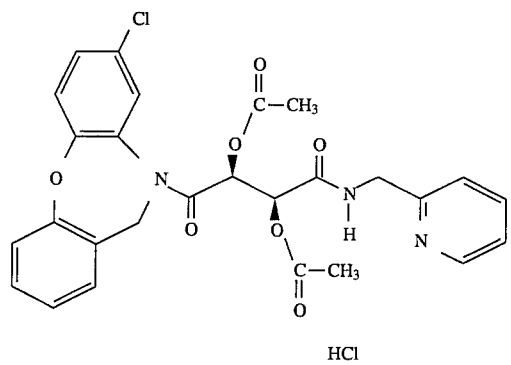

HCl

The procedure of Example 3 was repeated using 2-(aminomethyl)pyridine in the place of 4-(aminomethyl)pyridine to obtain the title compound as a white solid.

¹H NMR (200 MHz, DMSO-$d_6$) 1.70 (broad, distorted singlet, 3H), 2.08 (broad, distorted singlet, 3H), 4.36–6.09 (complex, 6H), 7.05–7.81 (complex, 9H), 8.40 (broad singlet, 1H), 8.78 (broad, singlet, 1H), 9.05. 9.22, 9.56 (three broad singlets, 1H total).

Elemental Analysis data for $C_{27}H_{24}ClN_3O_7$. 0.9 HCl. 1.0 $H_2O$

| Calculated | | Found |
|---|---|---|
| 55.08 | C | 55.23 |
| 4.61 | H | 4.24 |
| 7.14 | N | 7.06 |
| 11.44 | Cl | 11.49 |

EXAMPLE 6

αR,βR-Bis(acetyloxy)-8-chloro-γ-dibenz[b,f][1,4]-oxazepine-10(11H)-butanoic Acid

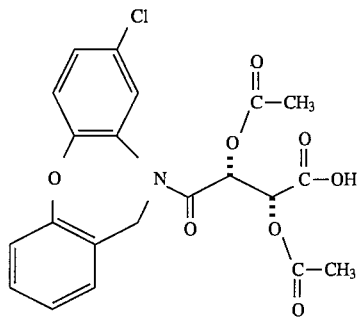

Diacetyl-L-tartaric anhydride is prepared from D-tartaric acid in the manner described in "DIACETYL-d-TARTARIC ANHYDRIDE (Tartaric anhydride, diacetate of d-)", *Organic Synthesis,* Collective Volume 4, 242–243 (1963). Briefly, a tartaric acid isomer or mixture of isomers is treated with acetic anhydride with a catalytic amount of sulfuric acid. The solution is heated gently for about 10 minutes and poured into an ice bath. The crystalline material formed is collected on a filter and is washed with toluene and ether and dried over phosphorus pentoxide and paraffin shavings. The crystalline bisacetyltartaric anhydride is used as is described in the following paragraph.

The procedure of Example 1 was repeated using diacetyl-L-tartaric anhydride in the place of diacetyl-D-tartaric anhydride to obtain the title compound as a white solid.

The NMR spectrum of the title compound was identical to the NMR spectrum of the product of Example 1.

EXAMPLE 7

αR,βR-Bis(acetyloxy)-8-chloro-γ-oxo-N-(4-pyridinylmethyl)dibenz[b,f][1,4]-oxazepine-10(11H) Hydrochloride

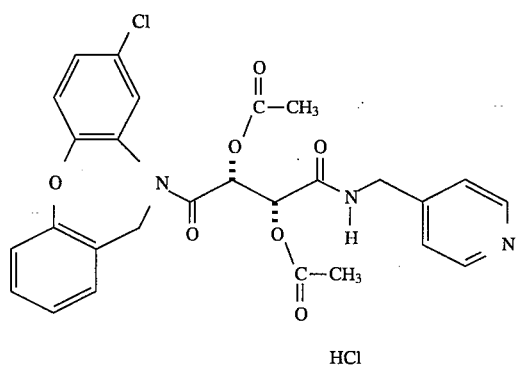

The procedure of Example 3 was repeated using the title product of Example 6 in the place of the title product of Example 1 to obtain the title compound as a white solid.

The NMR spectrum of the title compound was identical to the NMR spectrum of the title product of Example 3.

Elemental Analysis data for $C_{27}H_{24}ClN_3O_7$. 0.9 HCl. 1.5 $H_2O$

| Calculated | | Found |
|---|---|---|
| 54.25 | C | 54.20 |
| 4.70 | H | 4.36 |
| 7.03 | N | 6.95 |
| 11.27 | Cl | 11.29 |

EXAMPLE 8

αR,βR-Bis(acetyloxy)-8-chloro-γ-oxo-N-(3-pyridinylmethyl)dibenz[b,f][1,4]-oxazepine-10(11H) Hydrochloride

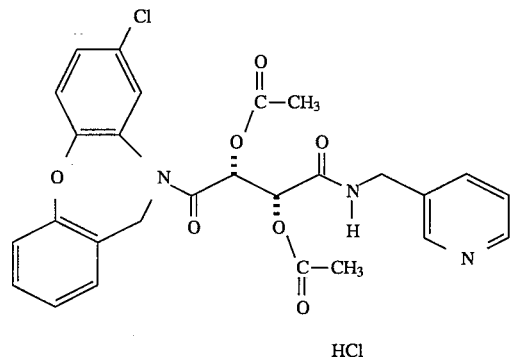

The procedure used to obtain the title product of Example 7 was applied in Example 8, with the exception that 3-aminomethylpyridine was replaced by 4-aminomethylpyridine to obtain the title compound as a white solid.

The NMR spectrum of the title compound was identical to the NMR spectrum of the title product of Example 4.

Elemental Analysis data for $C_{27}H_{24}ClN_3O_7 \cdot 0.9\ HCl \cdot 1.5\ H_2O$

| Calculated | | Found |
|---|---|---|
| 54.25 | C | 54.17 |
| 4.70 | H | 4.35 |
| 7.03 | N | 6.93 |
| 11.27 | Cl | 11.62 |

EXAMPLE 9

αR,βR-Bis(acetyloxy)-8-chloro-γ-oxo-N-(2-pyridinylmethyl)dibenz[b,f][1,4]-oxazepine-10(11H) Hydrochloride

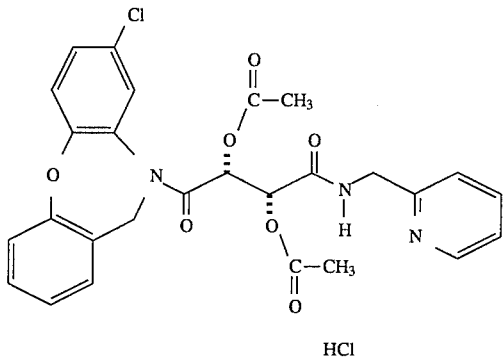

The procedure used to obtain the title product of Example 7 was applied in Example 9, with the exception that 2-aminomethylpyridine was replaced by 4-aminomethylpyridine to obtain the title compound as a white solid.

The NMR spectrum of the title compound was identical to the NMR spectrum of the title product of Example 5.

Elemental Analysis data for $C_{27}H_{24}ClN_3O_7 \cdot 0.9\ HCl \cdot 1.0\ H_2O$

| Calculated | | Found |
|---|---|---|
| 55.08 | C | 55.04 |
| 4.61 | H | 4.39 |
| 7.14 | N | 7.07 |
| 11.44 | Cl | 11.16 |

EXAMPLE 10

αS,βS-bis(acetyloxy)-γ-oxo-8-(trifluoromethyl)dibenz-[b,f][1,4]oxazepine-10(11H)-butanoic Acid

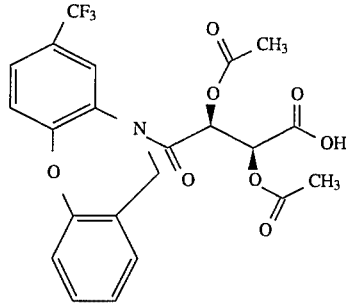

200 Parts of 4-chloro-3-nitrobenzo-trifluoride is heated to 160° C. and stirred and 160 parts of the potassium salt of salicylaldehyde is added over a period of 30 minutes. After the addition is complete, an exothermic reaction takes place and the temperature rises to about 195° C. Heating is then discontinued until the reaction subsides and the mixture is then heated for 1 hour at 150° C. The mixture is cooled, ice and water are added, and it is then extracted with ether. The ether layer is filtered to remove insoluble material and the resultant solution is dried over sodium sulfate. The ether solvent is then evaporated and the residual oil is recrystallized from a mixture of hexane and benzene to give 2-(2-nitro-4-trifluoromethylphenoxy)benzaldehyde melting at about 79°–81° C.

A solution of 55 parts of the ether obtained in the preceding paragraph in 800 parts of ethanol is hydrogenated over Raney nickel catalyst at room temperature and atmospheric pressure. When hydrogen uptake ceases the catalyst is removed by filtration and the ethanol solvent is evaporated. The residue is then dissolved in 500 parts by volume of hexane, filtered, and then cooled. There is then obtained yellowish-white crystals which are separated by filtration to give 8-trifluoromethyl-dibenz[b,f][1,4]oxazepine melting at about 86°–88° C.

The procedure of Example 1 is repeated using 8-trifluoromethyl-dibenz[b,f][1,4]oxazepine in the place of the 8-chloro-10,11-dihydrodibenz[b,f][1,4]oxazepine to produce the title compound.

EXAMPLE 11

αS,βS-bis
(acetloxy)-8-chloro-N-methyl-γ-oxo-N-(3-
pyridinylmethyl)dibenz[b,f][1,4]oxazepine-10(11H)-
butanamide

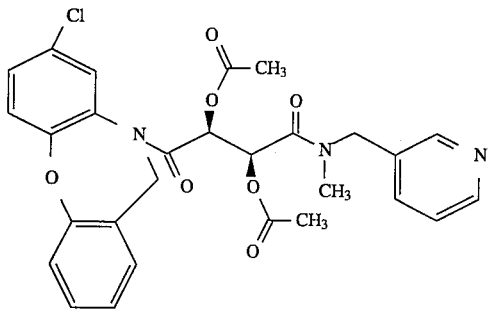

The procedure of Example 4 is repeated using 3-(N-methylaminomethyl)pyridine in the place of the 3-(aminomethyl)pyridine to produce the title compound.

The foregoing examples are provided to enable one of ordinary skill in the art to practice the present invention. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn,* 267, 131–140 (1984); C. Vander Wende et al., *Fed. Proc.,* 15, 494 (1956); Koster et al., *Fed. Proc.,* 18, 412 (1959); and Witken et al., *J. Pharmacol. exp. Ther.,* 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 hereinbelow.

Charles River male albino mice, weighing 20 to 30 grams, were used in this assay.

Thirty minutes after intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology,* 8, 191 (1974).

The results for the particular compounds of the present invention analyzed in this assay, and discussed in the examples identified below which correspond thereto, are presented in Table 1 hereinbelow as fractions under the heading "WRITHING ASSAY." The fractions indicate the number of mice out of ten in which a test compound produced analgesia.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A control dose response curve is produced in isolated segments of guinea pig ileum mounted in an automated apparatus with six concentrations of prostaglandin $E_2$. A solution or suspension of test compound is substituted for the control bathing solution and is incubated for thirty minutes. An additional prostaglandin $E_2$ dose response curve is then performed in the presence of the test compound. A dose ratio is calculated from the $EC_{50}$ values obtained from duplicate replications on each concentration of the test compound. A concentration of test compound is judged to be active if it produces a dose ratio significantly greater than that obtained in a series of blank treatments.

A dose ratio of $EC_{50}$ doses was calculated from the results of each test in a manner known by those of skill in the art, and described above.

The results of this prostaglandin antagonism assay are also presented in Table 1 hereinbelow. The compounds of the present invention which were tested in this assay, and for which results are presented in Table 1, correspond to the particular examples specified in Table 1.

TABLE 1

Data Generated from the Assays

| Example Number | WRITHING ASSAY I.G. | PGE ANTAGONISM IN GUINEA PIG ILEUM Dose Ratio |
|---|---|---|
| Example 2* | 0/10 | Not calculated |
| Example 3 | 5/10 | 1.3 |
| Example 4 | 9/10 | 0.74 |
| Example 5 | 5/10 | 1.7 |
| Example 7 | 8/10 | 1.2 |
| Example 8 | 6/10 | 2.4 |
| Example 9 | 5/10 | 1.1 |

*The compound shown and described in Example 2 is expected to produce analgesia in a mouse at a dose of this compound which is greater than 30 mg per kilogram of body weight.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A method for treating pain in an animal comprising administering to said animal a therapeutically-effective amount of a compound having a structure:

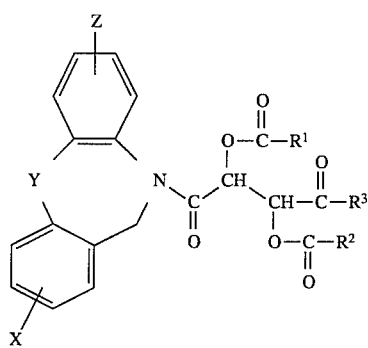

or a pharmaceutically-acceptable salt thereof, wherein:

X is hydrogen or halogen;

Y is oxygen, sulfur,

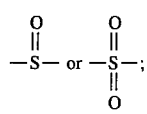

Z is hydrogen, halogen or -CF$_3$;

R$^1$, R$^2$ and R$^4$ may be the same or different, and are hydrogen or alkyl;

R$^3$ is —OH, —O-alkyl or —NR$^4$-alkylene-R$^5$; and

R$^5$ is —NR$^1$R$^2$ or aryl.

2. The method of claim 1 wherein the compound is:

αS,βS-Bis(acetyloxy)-8-chloro-γ-oxo-N-(4-pyridinylmethyl)-dibenz[b,f][1,4]oxazepine-10(11H) hydrochloride;

αS,βS-Bis(acetyloxy)-8-chloro-γ-oxo-N-(3-pyridinylmethyl)dibenz[b,f][1,4]oxazepine-10(11H)-butanamide, hydrochloride;

αS,βS-Bis(acetyloxy)-8-chloro-γ-oxo-N-(2-pyridinylmethyl)dibenz[b,f][1,4]oxazepine-10(11H)- hydrochloride;

αR,βR-Bis(acetyloxy)-8-chloro-γ-oxo-N-(4-pyridinylmethyl)dibenz[b,f][1,4]oxazepine-10(11H)- hydrochloride;

αR,βR-Bis(acetyloxy)-8-chloro-γ-oxo-N-(3-pyridinylmethyl)dibenz[b,f][1,4]oxazepine-10(11H)- hydrochloride; or αR,βR-Bis(acetyloxy)-8-chloro-γ-oxo-N-(2-pyridinylmethyl)dibenz[b,f][1,4]oxazepine-10(11H)- hydrochloride.

3. A method for treating prostaglandin-E$_2$ mediated diseases in an animal comprising administering to said animal a therapeutically-effective amount of a compound having a structure:

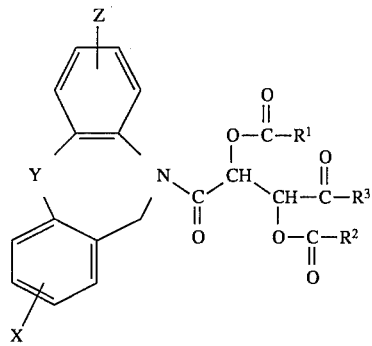

or a pharmaceutically-acceptable salt thereof, wherein:

X is hydrogen or halogen;

Y is oxygen, sulfur,

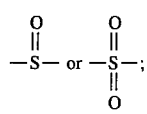

Z is hydrogen, halogen or —CF$_3$;

R$^1$, R$^2$ and R$^4$ may be the same or different, and are hydrogen or alkyl;

R$^3$ is —OH, —O-alkyl or —NR$^4$-alkylene-R$^5$; and

R$^5$ is —NR$^1$R$^2$ or aryl.

4. The method of claim 3 wherein the compound is:

αS,βS-Bis(acetyloxy)-8-chloro-γ-oxo-N-(4-pyridinylmethyl)-dibenz[b,f][1,4]oxazepine-10(11H) hydrochloride;

αS,βS-Bis(acetyloxy)-8-chloro-γ-oxo-N-(3-pyridinylmethyl)-dibenz[b,f][1,4]oxazepine-10(11H) hydrochloride;

αS,βS-Bis(acetyloxy)-8-chloro-γ-oxo-N-(2-pyridinylmethyl)dibenz[b,f][1,4]oxazepine-10(11H)- hydrochloride;

αR,βR-Bis(acetyloxy)-8-chloro-γ-oxo-N-(4-pyridinylmethyl)dibenz[b,f][1,4]oxazepine-10(11H)- hydrochloride;

αR,βR-Bis(acetyloxy)-8-chloro-γ-oxo-N-(3-pyridinylmethyl)dibenz[b,f][1,4]oxazepine-10(11H)- hydrochloride; or αR,βR-Bis(acetyloxy)-8-chloro-γ-oxo-N-(2-pyridinylmethyl)dibenz[b,f][1,4]oxazepine-10(11H)- hydrochloride.

* * * * *

UNITED STATES PATENT AND TRADEMARK OFFICE
CERTIFICATE OF CORRECTION

PATENT NO. : 5,604,220
DATED : February 18, 1997
INVENTOR(S) : NIZAL S. CHANDRAKUMAR ET AL.

Page 1 of 2

It is certified that error appears in the above-identified patent and that said Letters Patent is hereby corrected as shown below:

COLUMN 19

Line 5, "-10(11H)" should read ---10(11H)-butanamide,--;
Line 26, "(0,246 mL)" should read --(0.246 mL)--;
Line 28, "(0,226 mL)" should read --(0.226 mL)--.

COLUMN 20

Line 4, "-10(11H)" should read ---10(11H)-butanamide,--;
Line 45, "-10(11H)" should read ---10(11H)-butanamide,--.

COLUMN 22

Line 4, "-10(11H)" should read ---10(11H)-butanamide,--;
Line 43, "-10(11H)" should read ---10(11H)-butanamide,--.

COLUMN 23

Line 19, "-10(11H)" should read ---10(11H)-butanamide,-.

COLUMN 28

Line 13, "claim 1" should read --claim 1,--;
Line 16, "-10(11H) hydrochlo-" should read ---10(11H)-butanamide, hydrochlo---;
Line 22, "-10(11H) hydrochlo-" should read ---10(11H)-butanamide, hydrochlo---;
Line 25, "-10(11H) hydrochlo-" should read ---10(11H)-butanamide, hydrochlo---;
Line 28, "-10(11H) hydrochlo-" should read ---10(11H)-butanamide, hydrochlo---;
Line 31, "-10(11H) hydrochlo-" should read ---10(11H)-butanamide, hydrochlo---.

UNITED STATES PATENT AND TRADEMARK OFFICE
CERTIFICATE OF CORRECTION

PATENT NO. : 5,604,220

DATED : February 18, 1997

INVENTOR(S) : NIZAL S. CHANDRAKUMAR ET AL.

Page 2 of 2

It is certified that error appears in the above-identified patent and that said Letters Patent is hereby corrected as shown below:

COLUMN 29

Line 1, "claim 3" should read --claim 3,--;
Line 3, "-10(11H) hydrochlo-" should read ---10(11H)-butanamide, hydrochlo---;
Line 6, "-10(11H) hydrochlo-" should read ---10(11H)-butanamide, hydrochlo---;
Line 9, "-10(11H) hydrochlo-" should read ---10(11H)-butanamide, hydrochlo---.

COLUMN 30

Line 2, "-10(11H) hydrochlo-" should read ---10(11H)-butanamide, hydrochlo---;
Line 5, "-10(11H) hydrochlo-" should read ---10(11H)-butanamide, hydrochlo---;
Line 8, "-10(11H) hydrochlo-" should read ---10(11H)-butanamide, hydrochlo---.

Signed and Sealed this

Nineteenth Day of September, 2000

Q. TODD DICKINSON

*Attest:*

*Attesting Officer*

*Director of Patents and Trademarks*